United States Patent [19]

Shimatani

[11] 4,328,804

[45] May 11, 1982

[54] HYGIENIC TAMPON AND TAMPON APPLICATOR

[76] Inventor: Kazuo Shimatani, No. 249, Kamisoyagi, Yamato-shi, Kanagawa-ken, Japan

[21] Appl. No.: 94,657

[22] Filed: Nov. 15, 1979

[30] Foreign Application Priority Data

Nov. 16, 1978 [JP] Japan .......................... 53/158016[U]
Dec. 30, 1978 [JP] Japan .......................... 53/179198[U]

[51] Int. Cl.³ .............................................. A61F 13/20
[52] U.S. Cl. ..................................... 128/285; 28/118; 128/263
[58] Field of Search ..................... 128/285, 270, 263; 28/118

[56] References Cited

U.S. PATENT DOCUMENTS

| | | | |
|---|---|---|---|
| 2,734,505 | 2/1956 | Parish | 128/285 |
| 2,884,925 | 5/1959 | Meynier, Jr. | 128/285 |
| 2,926,667 | 3/1960 | Burger, Jr. et al. | 128/285 |
| 2,965,101 | 12/1960 | Schirmer et al. | 128/285 |
| 3,079,921 | 3/1963 | Brecht et al. | 128/285 |
| 3,369,544 | 2/1968 | Crockford | 128/285 |
| 3,520,302 | 7/1970 | Jones | 128/285 |
| 3,595,236 | 7/1971 | Corrigan et al. | 128/285 |
| 3,791,385 | 2/1974 | Davis et al. | 128/263 |

*Primary Examiner*—C. Fred Rosenbaum
*Attorney, Agent, or Firm*—McGlew and Tuttle

[57] ABSTRACT

A hygienic tampon and a tampon applicator. The tampon comprises a rope-shaped absorbent material coiled in parallel whirls and compressed into a bullet form and a withdrawal string attached to an end of the absorbent material. Because of the coiled structure, the tampon expands to all directions upon absorption of menstrual fluid to fully fill in the body cavity thereby preventing leakage. The expanded tampon can easily be withdrawn as the coiled tampon body is uncoiled when the withdrawl string is pulled. The tampon applicator comprises an outer tube for accomodation of a tampon therein and an inner tube telescopically engageable with the outer tube and operable to push the tampon out of the forward end of the outer tube and it is characterized in that a cap of water soluble material is detachably mounted on the forward end of the outer tube to cover the forward end and the head of the tampon. The water soluble cap assures smooth insertion of the tampon without pain.

6 Claims, 5 Drawing Figures

HYGIENIC TAMPON AND TAMPON APPLICATOR

BACKGROUND OF THE INVENTION

1. Field of the Invention

This invention relates to a hygenic tampon and a tampon applicator.

2. Description of the Prior Art

Various types of tampons have been proposed such as a pancake type, a bellow type or a rolled type. The pancake type tampon is made of a compressed flat material and its expansion rate is limited. Accordingly, it lacks in full absorption of menstrual fluid and is likely to lead to a leakage of the overflowing fluid. The bellow type tampon is made of a strip material folded and compressed in a zigzag manner and it is capable of expansion in the longitudinal direction upon absorption of menstrual fluid and thus has an increased absorption capacity. However, it does not expand sufficiently toward the vagina walls and accordingly it lacks the capacity for full absorption of fluid. The rolled type tampon is made of a flat material rolled and compressed to the form of a tampon and it is capable of expansion against the vagina walls upon absorption of fluid. However, it lacks a sufficient expansion in the longitudinal direction. Further, as it expands against the vagina walls, it becomes difficult to remove after use because of its frictional resistance against the vagina walls. When pulled by force, it turns around in the vagina and is thus liable to hurt the vagina walls.

On the other hand, a tube-type tampon applicator is known which comprises an outer tube for accomodation of a tampon and an inner tube telescopically engageable with the outer tube and operable to push the tampon out of the forward end of the outer tube into a body cavity. One of the problems with the tube-type applicator is that the forward end of the outer tube is likely to cause pain when it is inserted in the body cavity for ejection of the tampon. It has been proposed to overcome this problem by applying a lubricant to the forward end of the outer tube. However, the lubricant tends to be absorbed by the tube material whereby some lubricity is lost while giving the tube an unsanitary appearance. It has also been proposed to cover the forward end of the outer tube with a closure or a folded film sleeve which is adapted to be broken or forced open by the tampon when the tampon is ejected, e.g. as disclosed in U.S. Pat. No. 3,499,447. However, the manipulation of the applicator of this type has to be done with due care as the tampon is pushed against the resistance of the cover for ejection.

SUMMARY OF THE INVENTION

The present invention is intended to facilitate the use of hygienic tampons.

It is a primary object of the invention to provide a tampon having an adequate absorption capacity and which can easily be withdrawn after use. Thus, according to one aspect of the present invention a hygienic tampon is provided which comprises a rope-shaped absorbent material coiled in parallel whirls or turn and compressed into the form of a bullet and a withdrawal string attached to the rear end of the bullet form material. The shape of a bullet is used to mean a cylindrical shank with a rounded head. It will be understood that because of the coil structure, the tampon of the present invention expands in all directions upon absorption of menstrual fluid thus providing an increased absorption capacity and at the same time completely closing the body cavity whereby the possibility of leakage of the overflowing fluid is minimized. It will also be understood that the tampon can easily be withdrawn after use as it is uncoiled when it is pulled out.

It is another object of the invention to provide a tampon applicator which facilitates insertion of a tampon into a body cavity. Thus, according to another aspect of the invention, a tampon applicator is provided which comprises an outer tube for accomodation of a tampon and an inner tube telescopically engageable with the outer tube and operable to push the tampon out of the forward end of the outer tube into a vagina and which is characterised in that a cap made of a water soluble material acceptable for insertion into the body cavity is detachably mounted on the forward end of the outer tube to cover the forward end and, when the tampon is pushed into the vagina, to cap the head of the tampon. It will be understood that the water soluble cap of the present invention serves to cover the forward end of the applicator whereby the outer tube can be inserted into the body cavity without causing pain. It will also be understood that the water soluble cap also serves as a cap for the head of the tampon, which further facilitates insertion of the tampon into the vagina.

Other objects and advantages of the invention will become apparent from the following description of a preferred embodiment illustrated in the accompanying drawings.

DETAILED DESCRIPTION OF THE INVENTION

Figure 1:
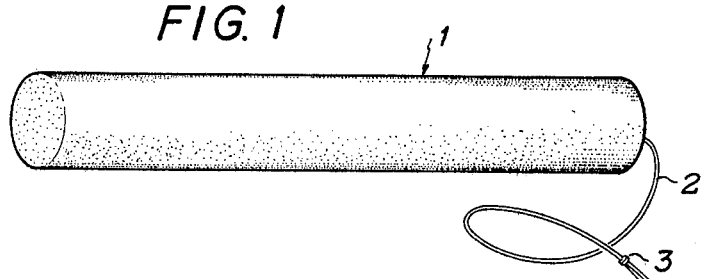
FIG. 1 is a perspective view of a rope-shaped absorbent material to be coiled and compressed to form a tampon of the present invention.

Referring to FIG. 1, numeral 1 designates a rope-shaped absorbent material which is made of cotton or other absorbent material such as paper. Elastic synthetic resins having a sponge structure with a high expansion rate may be incorporated in the rope-shaped material to improve its absorbency. The rope-shaped material may be made from a plurality of slender strips bundled together or spun together. It may not necessarily be round as illustrated, but may have an oval or angular cross-section.

Reference numeral 2 is a withdrawal string which is attached to one of the ends of the rope-shaped material. In order to increase a tensile strength of the absorbent material, the withdrawal string may be attached to the side of the rope-shaped absorbent material along the entire length of the side by stitching. Numeral 3 designates an adjuster for adjusting the length of the string. The adjuster illustrated is a ring type but it may be any other type.

Figure 2:
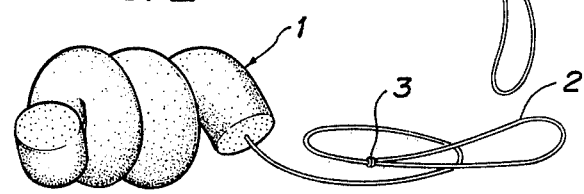
FIG. 2 is a perspective view of the same absorbent material which has been coiled but has not yet been compressed.

FIG. 2 shows the rope-shaped absorbent material 1 in a coiled state prior to compressing it into a bullet form. The absorbent material is coiled in parallel turn or whirls. The exact conditions for making the parallel whirls are determined depending on the nature of the material used and the operational conditions of the subsequent compressing step. However, in order to obtain a final product having an increased absorption effectiveness and which can easily be withdrawn after use from the vagina, the material should preferably be coiled mildly without tension in parallel turns with a little space between the adjacent whirls, and then it should firmly be compressed into a bullet form.

Figure 3:
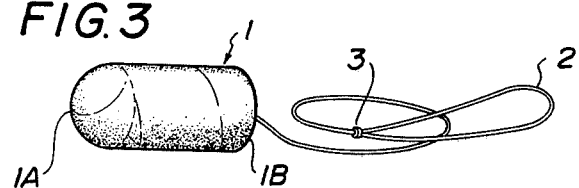
FIG. 3 is a perspective view of the tampon of the present invention which has been prepared by compressing the coiled absorbent material of FIG. 2 into a bullet form.

FIG. 3 shows a tampon of the present invention in a form of a bullet, which has been prepared by compressing the coiled absorbent material 1. The forward rounded end 1A of the tampon is made round for smooth insertion. The shank of the shape is substantially cylindrical or oval in cross-section.

Sample tampons have been prepared in three sizes i.e. a small size, a middle size and a large size, and their measurements as inserted in the applicators are as follows:

|  | Length (cm) | Volume (cm³) | Diameter (cm) |
|---|---|---|---|
| Small size | 5.0 | 5.0 | 1.2 |
| Middle size | 4.4 | 6.7 | 1.8 |
| Large size | 4.5 | 10.0 | 2.5 |

Their measurements as withdrawn after full expansion by absorption are as follows:

|  | Length (cm) | Volume (cm³) | Diameter (cm) |
|---|---|---|---|
| Small size | 12.3 | 15.0 | 1.2 |
| Middle size | 10.0 | 20.0 | 2.0 |
| Large size | 10.0 | 30.0 | 3.0 |

It should be noted that the volume increases upon absorption are as much as three times.

Figure 4:
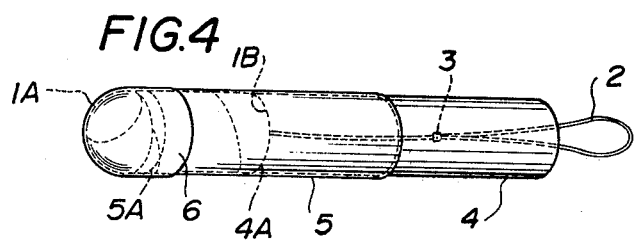
FIG. 4 is a perspective view of a tampon applicator of the invention with a tampon inserted therein and with a cap of a water soluble material mounted on the forward end thereof.
Figure 5:
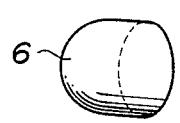
FIG. 5 is a perspective view of the water soluble cap of the invention.

FIG. 4 shows a tampon applicator of the present invention with a tampon of a bullet form inserted therein. The applicator comprises an outer tube 5 for accomodation of a tampon therein and an inner tube 4 telescopically engageable with the outer tube. Both tubes may be made of paper or the like. The inner tube 4 is operable to push the rear end 1B of the shank of the tampon with its forward end 4A for ejection of the tampon out of the forward end 5A of the outer tube 5. Numeral 6 in FIGS. 4 and 5 designates a cap made of a water soluble material acceptable for insertion in a vagina, such as polyethylene glycol or gelatin. The cap is disengageably mounted on the forward end 5A of the outer tube 5 to cover the forward end. The cap is also adapted to cap the head of the tampon when the latter is pushed into the vagina. As shown, the cap is preferably semispherical for smooth insertion. The cap, which is water soluble, may be left in the vagina and has no need to be taken out.

It should be noted that the cap covers not only the forward end of the outer tube for easy insertion of the latter without pain but also the head of the tampon for easy insertion of the tampon after it has been ejected from the forward end of the outer tube. This is particularly advantageous in that the cap prevents a premature expansion of the tampon which is otherwise likely to occur when the tampon absorbs menstrual fluid prematurely before it is inserted to a proper depth in the vagina.

Now, the manipulation of the applicator will be explained.

The forward end 5A of the outer tube 5 is inserted into a vaginal canal to a proper depth. Then, while holding the outer tube, the inner tube 4 is pushed forward thereby to push the tampon forward, whereupon the cap 6 is detached from the forward end of the outer tube 5 and the tampon is ejected from the forward end 5A into the vagina with the cap 6 on its head. The cap 6 is then dissolved in the menstrual fluid and absorbed by the tampon.

Thus, the tampon applicator of the present invention is so designed that the forward end 5A of the outer tube 5 is protected by the cap from direct contact with the vagina walls and the water soluble cap reduces frictional resistance and facilitates smooth insertion without pain.

Upon absorption of the menstrual fluid, the absorbent material expands to all direction because of the coiled structure. Thus, the body cavity is fully closed by the expanded tampon body whereby leakage is prevented. The expanded material has springy elastisty which permits a close contact of the tampon with the vagina walls, and which allows the user to move freely without the feeling of the existence of a foreign substance in her vagina. The expanded tampon body can easily be withdrawn from the vagina after use as the tampon body is uncoiled into a slender rope-shaped material when pulled by the withdrawal string 2. As the tampon of the present invention can easily be withdrawn, it is possible without fear to insert the tampon deep into the bottom of the vagina. The length of the withdrawal string is adjustable by the adjusting ring 3. An elastic material such as a sponge-like synthetic resin may be incorporated in the absorbent material to increase its elasticity. A tampon made of such elastic absorbent material has quick absorbency and can therefore be used conveniently when the menstrual fluid is extraordinarily abundant.

The water soluble cap ensures smooth insertion of a tampon without causing pain. Therefore, with the tampon applicator of the present invention, it is possible to insert a tampon of a larger size which has a greater absorption capacity and which is therefore suitable for use when the menstrual fluid is abundant.

It is understood that the invention is not to be construed as limited to the specific embodiment described above and that suitable changes, modifications and variations may be made without departing from the spirit and scope of the invention as defined in the appended claims.

What is claimed is:

1. A hygienic tampon comprising:
   a rope-shaped absorbent material having a length of about 10 to 12.3 cm, a diameter of about 1.2 to 3 cm and an uncompressed volume of about 15 to 30 cm³;
   the rope-shaped material being initially loosely coiled to form a single coil having unconnected parallel spaced turns and being thereafter compressed into the form of a shank having a rounded head end, with a withdrawal string attached to an opposite end of the rope-shaped absorbent material;

said shank being about 4.4 to 5.0 cm long, 1.2 to 2.5 cm in diameter and having a compressed volume of about 5 to 10 cm$^3$;

said shank expanding upon absorbing liquid and freely uncoiling to said uncompressed volume.

2. A hygienic tampon as claimed in claim 1 wherein an elastic synthetic resin having a sponge structure is incorporated in the absorbent material.

3. A hygienic tampon as claimed in claim 1 or 2 wherein the withdrawal string is adjustable in its length.

4. A tampon and applicator comprising:

an outer tube for accommodation of a hygienic tampon therein;

an inner tube telescopically engageable with the outer tube and operable to push the hygienic tampon out of the forward end of the outer tube into a vagina; and a rounded cap made of a water soluble material acceptable for insertion into the vagina, detachably mounted on the forward end of the outer tube to cover the forward end of the outer tube, and to cover a rounded head of the tampon;

the tampon comprising an initially rope-shaped absorbent material having a length of about 10 to 12.3 cm, a diameter of about 1.2 to 3 cm and an uncompressed volume of about 15 to 30 cm$^3$; the rope-shaped material being initially loosely coiled to form a single coil having unconnected parallel spaced turns and being thereafter compressed into the form of a shank having a rounded head end, with a withdrawal string attached to an opposite end of the rope-shaped absorbent material; said shank being about 4.4 to 5.0 cm long, 1.2 to 2.5 cm in diameter and having a compressed volume of about 5 to 10 cm$^3$; said shank forming the tampon with rounded disposed in said outer tube and expanding upon absorbing liquid in the vagina and freely uncoiling to uncompressed volume.

5. A tampon applicator as claimed in claim 4 wherein the cap is semispherical in shape.

6. A method of forming a hygienic tampon comprising:

providing a rope-shaped member of absorbent material having a length of about 10 to 12.3 cm, a diameter of about 1.2 to 3 cm and a volume of about 15 cm$^3$ to 30 cm$^3$;

loosely coiling the rope-shaped member without tension into a single helix having a plurality of unconnected spaced turns; and compressing the coiled rope-shaped member into a shape having a cylindrical shank and a rounded head which is from 4.4 to 5 cm long, 1.2 to 2.5 cm in diameter and 5 to 10 cm$^3$ in volume;

said coiled rope-shaped member adapted to absorb liquid and expand and uncoil to its uncompressed volume of about 15 to 30 cm$^3$.

* * * * *